United States Patent
Duschesne

(10) Patent No.: US 8,699,776 B2
(45) Date of Patent: Apr. 15, 2014

(54) METHODS AND APPARATUSES FOR QUANTITATIVELY DETERMINING THE LIKELIHOOD OF A DISEASE

(75) Inventor: Simon Duschesne, Quebec (CA)

(73) Assignee: Universite Laval, Quebec, QC (CA)

( * ) Notice: Subject to any disclaimer, the term of this patent is extended or adjusted under 35 U.S.C. 154(b) by 0 days.

(21) Appl. No.: 13/145,646

(22) PCT Filed: Feb. 8, 2010

(86) PCT No.: PCT/CA2010/000140
§ 371 (c)(1),
(2), (4) Date: Aug. 8, 2011

(87) PCT Pub. No.: WO2010/088763
PCT Pub. Date: Aug. 12, 2010

(65) Prior Publication Data
US 2012/0053447 A1    Mar. 1, 2012

Related U.S. Application Data

(60) Provisional application No. 61/150,723, filed on Feb. 6, 2009.

(51) Int. Cl.
*G06K 9/00*  (2006.01)
(52) U.S. Cl.
USPC ........... 382/132; 382/128; 382/131; 600/407; 600/410
(58) Field of Classification Search
USPC ............... 600/407–430, 437–469, 473–480; 382/128–132
See application file for complete search history.

(56) References Cited

U.S. PATENT DOCUMENTS

| | | | |
|---|---|---|---|
| 7,123,762 B2 | 10/2006 | Giger et al. | |
| 8,010,381 B2 * | 8/2011 | Sirohey et al. | 705/2 |
| 8,099,299 B2 * | 1/2012 | Sirohey et al. | 705/2 |
| 8,180,125 B2 * | 5/2012 | Avinash et al. | 382/128 |
| 2004/0015072 A1 * | 1/2004 | Pelletier et al. | 600/410 |
| 2004/0101181 A1 | 5/2004 | Giger et al. | |
| 2006/0104494 A1 | 5/2006 | Collins et al. | |
| 2006/0269115 A1 * | 11/2006 | Oosawa | 382/132 |

(Continued)

FOREIGN PATENT DOCUMENTS

WO    WO2005023086    3/2005

OTHER PUBLICATIONS

International preliminary report of PCT/CA2010/000140.
International search report of PCT/CA2010/000140.

(Continued)

*Primary Examiner* — Sanjay Cattungal
(74) *Attorney, Agent, or Firm* — Anglehart et al.

(57) ABSTRACT

The invention described provides a method of quantitatively evaluating one or more of the likelihood. severity and progression of a disease from medical images comprising processing medical images of a test subject to derive one or more feature space values characteristic of a disease-dependent image attributes, comparing the feature space values to those of a previously established database from medical images of known health} and known diseased subjects, wherein the comparing is based on feature space values that best discriminate between health and diseased subjects, summing a weighted distance of discriminant feature space values of the test subject to those of at least one of the mean feature space value of the healthy subjects and the mean feature space value of the diseased subjects, and providing from the summing a single number which is indicative of at least one of disease likelihood. severity and progression.

12 Claims, 6 Drawing Sheets

(56) References Cited

U.S. PATENT DOCUMENTS

| | | |
|---|---|---|
| 2007/0019846 A1 | 1/2007 | Bullitt et al. |
| 2009/0290772 A1* | 11/2009 | Avinash et al. ............... 382/130 |
| 2009/0292478 A1* | 11/2009 | Avinash et al. ................. 702/19 |
| 2009/0292551 A1* | 11/2009 | Sirohey et al. .................... 705/2 |
| 2009/0292557 A1* | 11/2009 | Sirohey et al. .................... 705/3 |
| 2010/0158334 A1* | 6/2010 | Martel-Pelletier et al. ... 382/131 |
| 2011/0129129 A1* | 6/2011 | Avinash et al. ............... 382/128 |
| 2011/0218405 A1* | 9/2011 | Avinash et al. ............... 600/300 |

OTHER PUBLICATIONS

Examination report and search report in EP 10738178.2 dated on Jun. 28, 2013 with related claims 1-14.

\* cited by examiner

METHODS AND APPARATUSES FOR QUANTITATIVELY DETERMINING THE LIKELIHOOD OF A DISEASE

TECHNICAL FIELD

The present invention relates to disease likelihood determination. More specifically, the invention relates to methods and apparatuses for the automated analysis of medical images for quantitatively evaluating the likelihood of a disease based on tissue attributes.

BACKGROUND

Early detection of certain diseases, such as Alzheimer's dementia (AD), is critical for treatment success and a high priority research area. The development of disease-modifying treatment strategies requires objective characterization techniques and in vivo quantitative biomarkers that are able to identify the disease with higher accuracy and at a much earlier stage than clinically based assessment (Vellas, B., et al., *Disease-modifying trials in Alzheimer's disease: a European task force consensus*. Lancet Neurol, 2007. 6(1): p. 56-62).

Medical images, and in particular standard magnetic resonance imaging (MRI) sequences (T1, T2 or PD-weighted) on 1 to 3 Tesla clinical scanners, can show pathologically related changes in cortical and sub-cortical structures (Csernansky, J. G., et al., *Correlations between antemortem hippocampal volume and postmortem neuropathology in AD subjects*. Alzheimer Dis Assoc Disord, 2004. 18(4): p. 190-5; Kloppel, S., et al., *Automatic classification of MR scans in Alzheimer's disease*. Brain, 2008). Global, regional and local cerebral morphology alterations, such as tissue atrophy, are reflections of the microscopic disease progression. Analysis of structural MRI allows the in vivo assessment of these changes, and therefore can be used as a quantitative biomarker in AD (Weiner, M., et al., *The Use of MRI and PET or Clinical Diagnosis of Dementia and Investigation of Cognitive Impairment: A Consensus Report*. 2005, Alzheimer's Association; Chetelat, G. and J. C. Baron, *Early diagnosis of Alzheimer's disease: contribution of structural neuroimaging*. Neuroimage, 2003. 18(2): p. 525-41; Davatzikos, C., et al., *Detection of prodromal Alzheimer's disease via pattern classification of magnetic resonance imaging*. Neurobiol Aging, 2008. 29(4): p. 514-23).

In previous work (Duchesne, S., et al., *MRI-Based Automated Computer Classification of Probable AD Versus Normal Controls*. IEEE Trans Med Imaging, 2008. 27(4): p. 509-20. [7]), applicants developed a novel, high-dimensional classification approach based on data reduction techniques of MRI image attributes, defined as the combination of intensity and shape characteristics. The technique was tested in a series of pilot studies that used single-time point T1w MRI for the differentiation of normal aging from AD.

Due to the important human and financial costs of certain diseases (e.g. Alzheimer's), an automated quantitative biomarker enabling effective and early disease identification, based on medical image data, would permit earlier treatment initiation and be useful to reduce patient suffering and costs to primary caregivers and health care systems.

SUMMARY OF THE INVENTION

Applicants have discovered that the analysis of MRI data, relating to brain morphological characteristics such as tissue compositions and deformations in the context of AD research, in combination with appropriate statistical distance-based calculations to calculate group-wise membership, allows for the determination of a single quantitative metric that applicants have coined the Disease Evaluation Factor (DEF) and the Disease likelihood factor (DLF). The DEF and DLF can be determined using Applicants classification system presented in US Pub. No. 2006/0104494. This method allows for the generation of an eigenspace representation of images from two or more groups of subjects, for example healthy and diseased subjects. From this eigenspace, the most discriminant eigenvectors are selected and subsequently used in order to increase the specificity and sensitivity of the discrimination function. The DEF and DLF provide a scalar number that estimates disease likelihood and/or severity and/or progression.

Applicants have tested the efficiency of the DLF and DEF at estimating disease burden in normal, control subjects (CTRL), probable AD patients, and subjects with Mild Cognitive Impairment (MCI), a putative prodromal stage of AD. Applicants hypothesize that the DEF and DLF can accurately describe disease status via automated analysis of multivariate MRI-based image attribute data.

It is an object of the present invention to provide a method of quantitatively evaluating the likelihood and/or severity of a disease from medical images comprising: processing medical images of a test subject to derive one or more feature space values characteristic of a disease-dependent image attributes; comparing the feature space values to those of a previously established database from medical images of known healthy and known diseased subjects, wherein the comparing is based on feature space values that best discriminate between healthy and diseased subjects; summing a weighted distance of discriminant feature space values of the test subject to those of at least one of the mean feature space value of the healthy subjects and the mean feature space value of the diseased subjects; and providing from the summing a single number which is indicative of at least one of disease likelihood, severity and progression.

In some embodiments, the weighted distance further comprises an attraction field calculation wherein each feature space value of a test subject is attracted to the mean feature space value of healthy and mean feature space value of diseased subjects as a function of its distance from each and according to the gravitational model formula presented herein (equations 7 and 8).

It is yet another object of the present invention to provide a method of quantitatively evaluating the likelihood of progression of a disease from medical images by providing a single number indicative of said likelihood. In some embodiments, this progression will be the progression from MCI to AD.

It is yet another object of the present invention to provide a system for quantitatively evaluating the likelihood and severity of a disease from medical images comprising an image processor receiving as input a medical image of a test subject and processing the medical image to derive one or more feature space values characteristic of a disease-dependent tissue morphology; a processor comparing the feature space values to those of a previously established database from medical images of known healthy and known diseased subjects; wherein the comparing is based on feature space values that best discriminate between healthy and diseased subjects; a processor summing a weighted distance of all discriminant feature space values of the test subject to those of at least one of the mean feature space value of the healthy subjects and the mean feature space value of the diseased subjects; and a calculator providing from the sum a single number which is indicative of disease likelihood and severity.

BRIEF DESCRIPTION OF THE DRAWINGS

The invention will be better understood by way of the following detailed description of a preferred embodiment, with reference to the appended drawings, in which.

DETAILED DESCRIPTION

Figure 1:
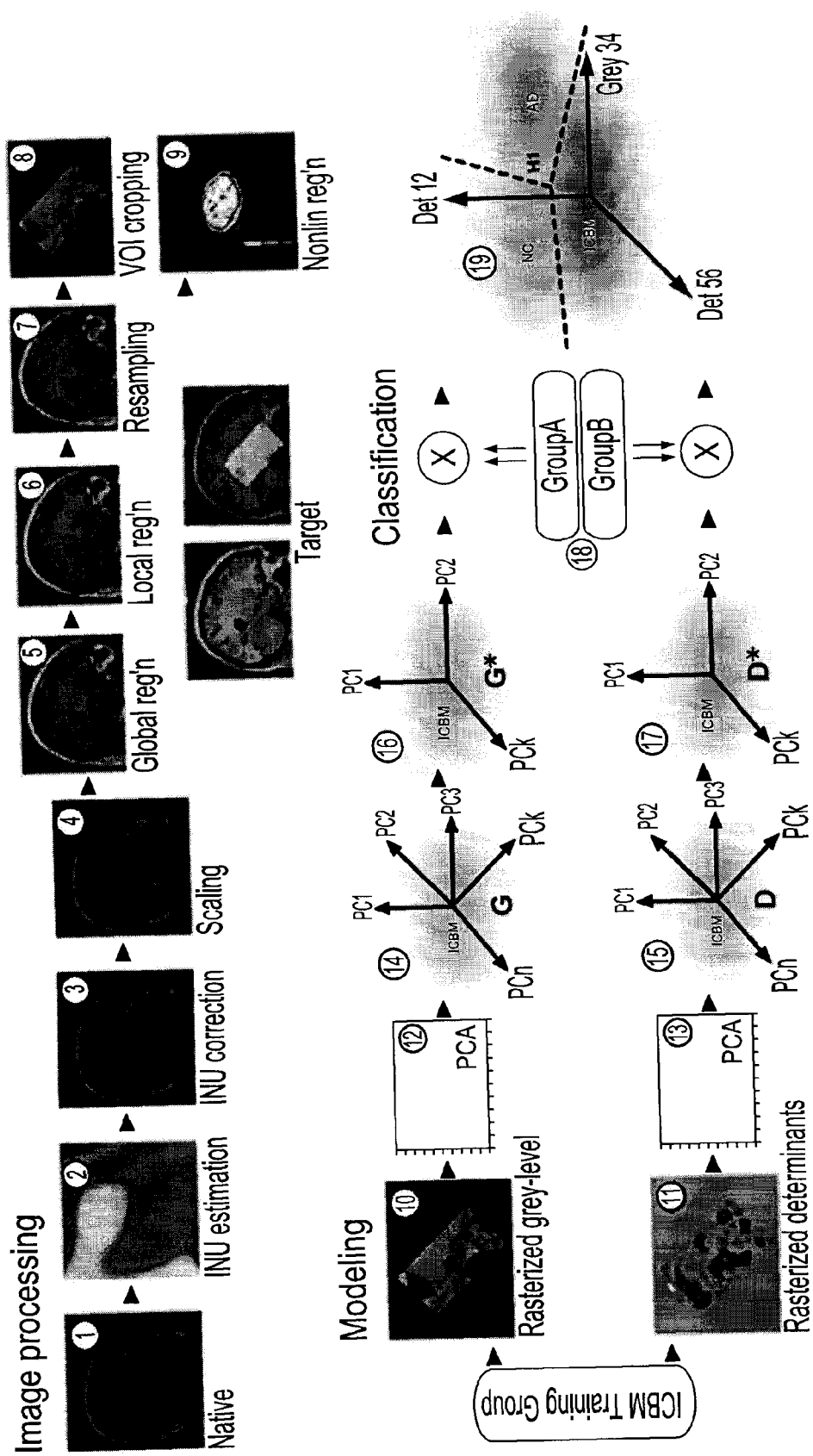
FIG. 1 is a schematic representation of an automated image processing pipeline.

Subjects. A total of 349 subjects were included in this study. The first cohort, or reference group, consisted in 149 young, neurologically healthy individuals from the ICBM database (Mazziotta, J. C., et al., *A probabilistic atlas of the human brain: theory and rationale for its development. The International Consortium for Brain Mapping (ICBM)*. Neuroimage, 1995. 2(2): p. 89-101), whose scans were used to create the reference space.

The second cohort, or study group, consisted in 150 subjects: 75 patients with a diagnosis of probable AD and 75 age-matched normal CTRL without neurological or neuropsychological deficit. The probable AD subjects were individuals with mild to moderate probable AD (McKhann, G., et al., *Clinical diagnosis of Alzheimer's disease: report of the NINCDS-ADRDA Work Group under the auspices of Department of Health and Human Services Task Force on Alzheimer's Disease*. Neurology, 1984. 34(7): p. 939-44) recruited among outpatients seen at the Centro San Giovanni di Dio Fatebenefratelli—The National Center for AD (Brescia, Italy) between November 2002 and January 2005. CTRL subjects were taken from an ongoing study of the structural features of normal aging.

The third cohort consisted in 49 MCI subjects taken from a prospective project on the natural history of MCI, carried out in the same memory clinic. All MCI patients underwent a yearly follow-up visit, consisting of complete clinical and neuropsychological examination, from 1 to 4 years after enrolment. In those individuals that converted to dementia, status was ascertained according to clinical diagnostic criteria for AD, subcortical vascular dementia, dementia with Lewy bodies, and fronto-temporal dementia. Within the larger prospective cohort of 100 MCI patients enrolled from April 2002 to December 2006, Applicants have selected patients retrospectively for this study based on their (a) having been followed clinically a minimum of 48 months after their baseline MR scan; and (b) having remained either stable (MCI-S group; N=29) or progressed to probable AD (MCI-P group; N=20; mean progression 1.5 yrs; SD 0.7 yrs). The 48-month longitudinal clinical evaluation constitutes our reference diagnostic.

Data for the last subject was obtained with permission from the pilot, multi-centric European ADNI project [15](E-ADNI). It consisted in a healthy volunteer that acted as human quality control phantoms and that was scanned three times at The Anonymous Center (scan; repeat scan, same session; rescan) on the same day.

Ethics Committees approved the study and informed consent was obtained from all participants.

MR Data. The ICBM subjects from the reference group were scanned in Montreal, Canada on a Philips Gyroscan 1.5T scanner (Best, Netherlands) using a T1-weighted fast gradient echo sequence (sagittal acquisition, TR=18 ms, TE=10 ms, 1 mm×1 mm×1 mm voxels, flip angle 30°). MRI data for all subjects in the probable AD, CTRL and MCI study group were acquired in Brescia, Italy on a single Philips Gyroscan 1.0T scanner (Best, Netherlands) using a T1-weighted fast field echo sequence (sagittal acquisition, TR=25 ms, TE=6.9 ms, 1 mm×1 mm×1.3 mm voxels).

Image Processing. A cursory overview of the automated image processing methodology follows; the reader is referred to Duchesne et al. (see Duchesne et al. 2008) for additional details, as well as to US patent application publication 2006/0104494 published on May 18, 2006, the specification of which is hereby incorporated by reference. Images from all reference and study subjects were processed in an identical fashion. Processing included intensity non uniformity correction, scaling, global and linear registration, extraction of a pre-determined volume of interest centered on the medial temporal lobes, nonlinear registration within the volume of interest towards a common reference target, and computation of the determinants from the Jacobian of the deformation field (see FIG. 1 for a schematic diagram of data processing used). Image processing and other data processing in accordance with the present embodiments can be performed using a conventional computer or workstation configured with computer program modules for performing the data processing as set out herein.

DEF Processing Overview. The basic processing steps are: processing the medical image of the study patient's tissue to derive one or more feature space values characteristic of disease-dependent tissue morphology; computing a single disease evaluation factor (DEF) from the feature space values of the study patient and those of reference subjects.

Applicants propose a single factor that estimates disease state in a given individual, and that can be repeated at any time point; the larger the index, the more severe the condition. Applicants calculated a reference eigenspace of MRI image attributes from reference data, in which CTRL, probable AD and MCI subjects were projected. For the purpose of calculating the DEF between CTRL and probable AD, Applicants then calculated the multi-dimensional hyperplane separating the CTRL and probable AD groups. The DEF was estimated via a multidimensional weighted distance of eigencoordinates for a given subject (feature space distance) and the CTRL group mean, along salient principal components forming the separating hyperplane. The directionality was defined towards the center of the probable AD group, and each distance was weighted by a coefficient for that particular component. Applicants used quantile plots, Kolmogorov-Smirnov and $\chi^2$ tests to compare the DEF or DLF values and test that their distribution was normal. Applicants used a linear discriminant test to separate CTRL from probable AD based on the DEF or DLF, and reached an accuracy of 90%.

In some embodiments, the disease evaluation factor is calculated using attraction field formulations, yielding "attraction" values between the study patient's feature space values and the mean values of groups of reference subjects. In other embodiments, the DEF or DLF is calculated using a likelihood ratio.

DEF. The features for each subject i that were used for modeling are: 1) the scaled, intensity-uniformity corrected T1-weighted intensity rasterized data vectors $g_i$ within the volume of interest, post-linear registration; and 2) rasterized vector $d_i$ of determinant values within the volume of interest, post-nonlinear registration. Principal components analysis (PCA) was used to reduce the dimensionality of this massive amount of data (405,000 voxel for each $g_i$ or $d_i$ feature) and build a model of grey-level intensity and determinant eigenvectors from the reference data, composed of N=149 healthy young subjects from the ICBM reference group. The resulting ensemble of p Principal Components, where p=N−1, defined an Allowable Grey-Level Domain G and Allowable Determinant Domain D as the spaces of all possible elements expressed by the determinant eigenvectors $\lambda_G$; and $\lambda_D$. In those spaces most of the variation can usually be explained by a smaller number of modes, l, where l<<n and l<p. The total variance of all the variables is equal to:

$$\lambda = \sum_{k=1}^{2n} \lambda_k \quad (1)$$

whereas for l eigenvectors, explaining a sufficiently large proportion of $\lambda$, the sum of their variances, or how much these principal directions contribute in the description of the total variance of the system, is calculated with the ratio of relative importance of the eigenvalue $\lambda_k$ associated with the eigenvector k:

$$r_k = \frac{\lambda_k}{\sum_{j=1}^{p} \lambda_j}. \quad (2)$$

The theoretical upper-bound on the dimensionality f of G and D is N−1 however, Applicants defined restricted versions of these spaces denoted G* and D*, using only the first k eigenvectors corresponding to a given ratio r for each space. The reference group data was no longer used after this point.

Once the model eigenspaces G* and D* from reference data have been formed, Applicants proceeded with the task of projecting the rasterized image attribute vectors $i_i$ and $d_i$ for the subjects in the study group into the space defined by the reference group. The projected data in the Domain G* formed the eigencoordinate vectors $\gamma_i^{\omega}$; likewise, projected data into the Domain D* forms the eigencoordinate vectors $\delta_i^{\omega}$.

Applicants created data boxplot to get an idea of distribution normality. The boxplot shows the asymmetry and outliers for each variable, which allows Applicants, without formal testing, to assess if some variables are not-normal, and hence if the ensemble of projection data is not multi-normal.

One of the assumptions of discriminant analysis is that the populations are distributed according to a multivariate normal distribution, with equal matrices of variances-covariances. Otherwise, for non-normal distributions, Applicants might consider using logistic regression analysis; and in the cases where the matrices of variances-covariances are significantly different, one can use quadratic discriminant analysis.

Following the notation of Duda et al. (Duda, R. O., P. E. Hart, and D. G. Stork, *Pattern Classification* 2001: Wiley-Interscience), Applicants defined two states of nature $\omega$ for our study subjects, e.g. for the purpose of discriminating CTRL from probable AD: $\omega_{CTRL}$=CTRL, and $\omega_{AD}$=probable AD. For the purposes of this work, the prior probabilities $p(\omega_{CTRL})$, $p(\omega_{AD})$ were known equal (p=0.5; p=0.5) since the compositions of the classification data sets were determined. It must be stated that they do not represent the normal incidence rates of probable AD in the general population. Applicants used the vectors $\gamma_i^{\omega}$ and $\delta_i^{\omega}$ as feature vectors in a system of supervised linear classifiers.

The data was first normalized to guard against variables with larger variance that might otherwise dominate the classification. Applicants employed forward stepwise regression analysis via Wilk's $\lambda$ method to select the set of discriminating variables $\{\lambda_f\}$, with f<<N−1, forming the discriminating hyperplane. Applicants then verified the multinormality of the ensemble of vectors retained in the final classification function.

Distances and weighting. In our image-based feature space, the distance d can be calculated in a number of different fashions (Manhattan, Euclidean, Mahalanobis, Kullback-Leibler), see for example Duda, R. O., P. E. Hart, and D. G. Stork, *Pattern Classification* 2001, New York, N.Y., USA: Wiley-Interscience). Using the restricted set $\{\lambda_F\}$, Applicants defined the DEF or DLF as the multidimensional distance between each subject and the center of the CTRL group, denoted $\overline{m}_{CTRL}$.

Manhattan distance. As a distance, Applicants propose initially the signed difference between subject eigencoordinates along the eigenvector $\lambda_F$ and the CTRL mean for that eigenvector. This difference shows the magnitude and direction from the subject to the mean of a group of control subjects:

$$d_i^{\lambda_F} = x_i^{\lambda_F} - \overline{m}_{CTRL}^{\lambda_F} \quad (3)$$

Euclidean distance. Applicants propose the Euclidean distance between position $p_i$ of each subject $s_i$ and both CTRL and probable AD means along the restricted set of eigenvectors $\{\lambda_F\}$ in all F directions, with F<<N−1. As the distance to one center decreases, the distance to the second should increase. In the equation, applicants demonstrate the distance to the mean of the probable AD group:

$$d_{s_i \to CM_{AD}} = \sqrt{\sum_F \left(p_i^f - \overline{m}_{AD}^f\right)^2} \quad (4)$$

Weighted distance. It is possible to weigh each eigenvector by an associated measure of significance, for example Wilk's $\lambda$ from the stepwise regression analysis or a factor derived from univariate t-tests. While the Wilk's $\lambda$ is trivially obtained from the regression analysis, an univariate weight such as the Koikkalainen factor formulation (Koikkalainen, J., et al. Estimation of disease state using statistical information from medical imaging data. in Medical Image Computing and Computer Assisted Intervention—From statistical atlases to personalized models workshop. 2006. Copenhagen, Denmark: MICCAI Society) entails performing a t-test comparing the group eigencoordinate distributions (e.g. CTRL vs. probable AD; MCI-S vs. MCI-P) for each eigenvector of the restricted set, resulting in the p-value $p(\lambda_F)$ for that distribution; from these p-values the significance weight SF was calculated:

$$S_F = \frac{\ln \min[p(\lambda_F), 0.05] - \ln 0.05}{\ln 0.000001 - \ln 0.05}. \quad (5)$$

The significance increases as the differences between the CTRL and AD groups grows, and reaches zero when there are no statistically significant difference (at the p=0.05 level) between both distributions. The resulting weighted distance Di combines the aforementioned distances (Manhattan, Euclidean) with a weight SF (either Wilk's $\lambda$, or Koikkalainen factor) over all eigenvectors F from the restricted set $\{\lambda_F\}$ as follows:

$$D_i = \frac{\sum_{\lambda_F}^{\lambda_F} S_F d_i^{\lambda_F}}{\sum_{\lambda_F} S_F}. \quad (6)$$

Gravitational model. As the final formulation, Applicants extend the principle of image-based distance to the context of an attraction field that follows Newton's Law of Universal Gravitation, whereby any two elements of mass m within the feature space will exert upon one another an attractive force that will vary proportionally to the inverse of the square of the distance between them. In our context the force exerted by one group (e.g. CTRL) decreases as the distance between a subject and the center of mass of the CTRL group grows, while the force exerted by the second group (e.g. probable AD) increases as distance decreases between the same subject and the second group's center of mass. In a multiple group scenario, the calculated combined force serves as a quantitative measure of the likelihood of belonging to one of the groups.

In such a classical formulation the force between any subject $s_i$ with mass $m_i$, to the centers of mass of e.g. the CTRL group ($CM_{CTRL}$) and the AD group ($CM_{AD}$), is expressed as:

$$F_{s_i \to CTRL, AD} = Gm_i \left( \frac{CM_{CTRL}}{d_{s_i \to CM_{CTRL}}^2} - \frac{CM_{AD}}{d_{s_i \to CM_{AD}}^2} \right) \quad (7)$$

with $$CM = \frac{1}{M} \sum_i m_i p_i \quad (8)$$

being the formulation for the centers of mass calculations, where M is the total mass for all subjects in the group, $m_i$ their individual masses, and $p_i$ their individual positions in feature space as derived in the previous section. The distance metric that can be used can be anyone of the aforementioned distances; for the purposes of the current study, the Euclidean distance as formulated in Eq. 3 was employed.

Applicants chose to retain the concept of "mass" even though it has no real bearing within the present context of an image-based feature space. It could be replaced with different information regarding individuals in the groups, for example Braak histopathological staging. Alternatively one can vary the specificity and sensitivity of the attraction field by increasing the "mass" of subjects in one of the groups (e.g. CTRL or probable AD). For these purposes however Applicants set the mass of each subject to unity, and, further, for equal considerations of simplicity, Applicants set the gravitational constant G also to unity.

Statistics and measurements were computed using the MATLAB Statistics Toolbox (The MathWorks, Natick, Mass.).

Demographics. There were no statistically significant differences for age between the 75 probable AD (mean=73.3 yrs: SD=8.4 yrs) and 75 NC individuals (mean=73.3 yrs: SD=4.6 yrs) (Student's T test, DF=148, P>0.05). There was a statistical difference for age (Student's T test, DF=47, p=0.001) between the MCI-S (mean=74.2 yrs: SD=6.4 yrs) and MCI-P groups (mean=63.6 yrs: SD=14.2 yrs).

Data processing and feature selection. Applicants set the variance ratio r (see eq. (2)) to 0.997, resulting in a PCA model composed of 112 $\lambda_G$ eigenvectors spanning Domain G* and 144 $\lambda_D$ eigenvectors spanning Domain D*. Applicants have not performed a sensitivity analysis of the DEF or DLF results for different values of r.

Using this data Applicants proceeded with forward stepwise regression analysis using Wilk's $\lambda$ method (P-to-enter=0.005) to select the discriminating variables forming the separating hyperplane. This was performed in a leave-one-out fashion to eliminate over-learning of the dataset. To select the final, restricted set of eigenvectors $\lambda_F$, Applicants selected the eigenvectors that were present in the discriminating eigenplane for 99% of cases, which resulted in 3 eigenvectors. This is an empirical approach to feature selection: ideally, the current dataset would be used solely for training and not testing. Applicants have not performed a sensitivity analysis on this threshold.

Figure 2:
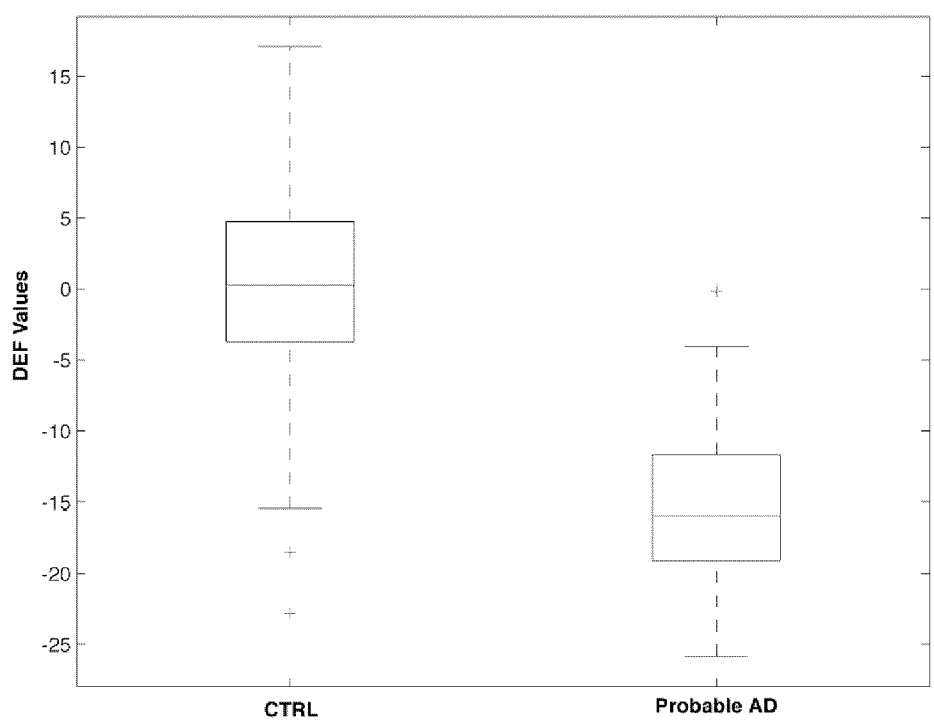
FIG. 2 is a graphical view of DEF scores for CTRL (left) and probable AD (right).
Figure 3:
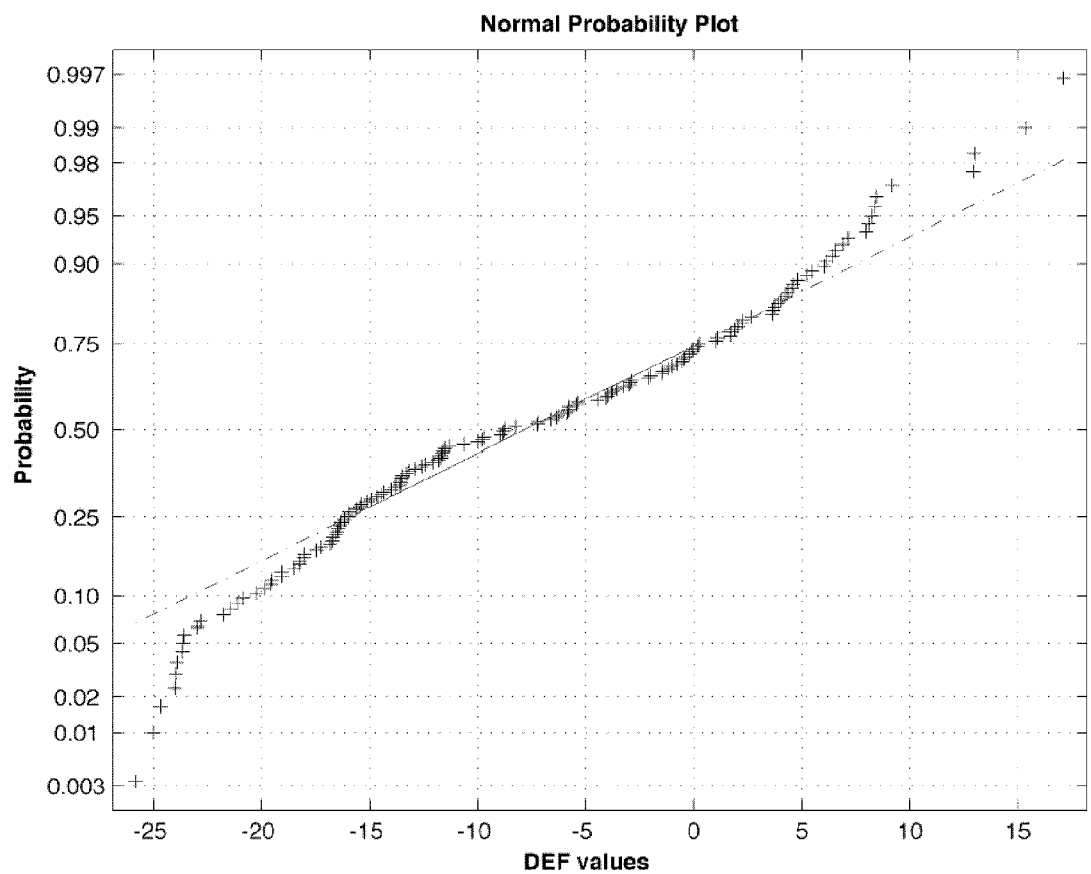
FIG. 3 is normal probability plot of CTRL and probable AD DEF scores.

DEF calculation for CTRL vs Probable AD. A second leave-one-out loop was performed to calculate the DEF. For each instance of the loop, the CTRL mean $\overline{m}_{CTRL}$ and significance weights $S_F$ were calculated independently of the test subject. The distances and the DEF were then computed for that individual (FIG. 2). The process was repeated 150 times. Applicants used quantile plots, Kolmogorov-Smirnov (p<0.0001) and $\chi^2$ (p=0.0019) tests to compare the DEF values and test that their distribution was normal (FIG. 3). Applicants used a linear discriminant test to separate CTRL from probable AD based on the DEF factor, which reached an accuracy of 90% (see below). Statistics and measurements were computed for the data set used in the above example using the MATLAB Statistics Toolbox (The MathWorks, Natick, Mass.).

a) Comparing the Accuracy of Different Models:
  Manhattan distance: 0.78
  Euclidean distance: 0.73
  Wilk's $\lambda$: 0.85
  Koikkaleinen weighted distance: 0.86
  Gravitational model: 0.90

It will be appreciated that an attraction field formulation is not limited to the classical gravitational formula used in this example.

b) On the Topic of Masses:

It is possible to vary the masses in order to increase/decrease the sensitivity/specificity of the model. Basically, if one allows the "CTRL" to weight "more", then the pull would be greater, and hence, one will increase sensitivity at the expense of specificity (one would classify more people as CTRL, but the AD would be "truer" AD). The logic applies in reverse.

Applicants therefore have ran experiments by varying the mass of subjects in either groups, e.g. assigning a weight of 2.0, 3.0, 4.0 to CTRL and then to AD. As predicted, the sensitivity/specificity varies, the best result was with a CTRL=2.0 mass, at which accuracy fell marginally to 0.87 but sensitivity went up to 0.89.

DEF Calculations for MCI-P Vs MCI-NP

Figure 4:
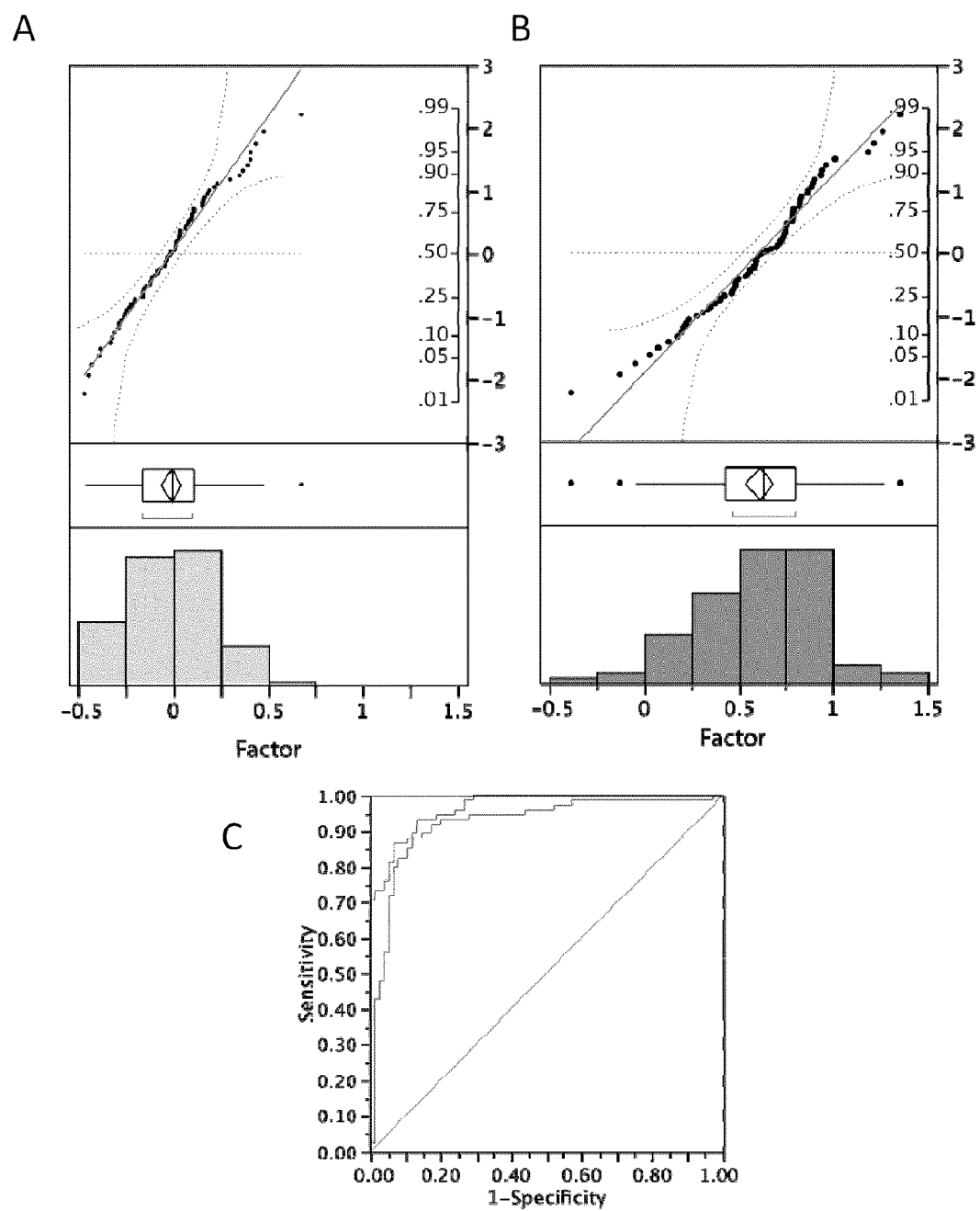
FIG. 4 is a graphical view of the distribution of morphological factors for the CTRL (A) and probable AD groups (B) as well as the ROC curves for sensitivity vs specificity (C).
Figure 5:
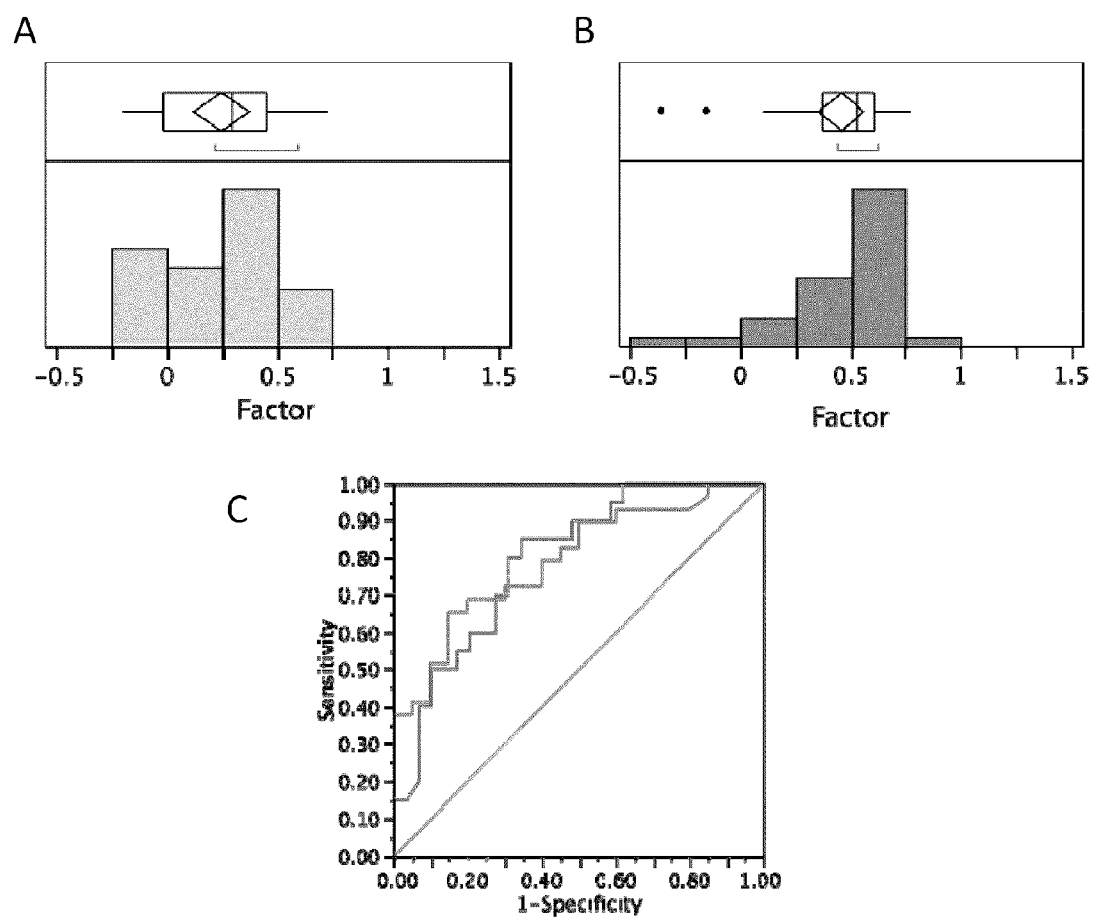
FIG. 5 is a graphical view of the distribution of morphological factors for the MCI-S (A) and MCI-P groups (B) as well as the ROC curves for sensitivity vs specificity (C).

Using the Gravitational model, Applicants report the results for the morphological factor for the CTRL vs. probable AD experiment and the MCI-S vs. MCI-P experiment in Table 1. The distributions of morphological factors for all groups, alongside quantile plots to assess normality (CTRL and probable AD groups) are shown in FIGS. 4 and 5.

Distributions of DEF for the CTRL and probable AD groups alongside quantile plots based on the Gravitational model are shown in FIGS. 4A and 4B. Receiver operating characteristic curve (ROC) for the morphological factor displaying the trade-offs between sensitivity and specificity at the task of discriminating CTRL vs. probable AD are shown in FIG. 4C. The Area under the ROC curve was 0.9444. At the 90% accuracy point (135/150), specificity was 87.5% and sensitivity 92.9%.

TABLE 1

|  | CTRL | AD | MCI Stable | MCI Progressed |
|---|---|---|---|---|
| N | 75 | 75 | 29 | 20 |
| Mean | 0.61 | −0.01 | 0.45 | 0.24 |
| Std Dev | 0.32 | 0.23 | 0.26 | 0.27 |
| Std Err Mean | 0.04 | 0.03 | 0.05 | 0.06 |
| Upper 95% Mean | 0.68 | 0.04 | 0.55 | 0.37 |
| Lower 95% Mean | 0.53 | −0.06 | 0.35 | 0.12 |

With the Gravitational model Applicants computed the ROC curve for the discrimination of MCI-S (FIG. 5A) from MCI-P (FIG. 5B). The Area under the ROC curve (FIG. 5C) was 0.7940. At 72.3% accuracy, specificity was 62%, and sensitivity 75%.

DEF calculations for E-ADNI. Applicants then computed the morphological factor for the E-ADNI human phantom volunteer, using the CTRL and probable AD cohorts as a training group (for the determination of the discriminating function). Using the Gravitational model, the average factor value was −0.4, or 4 standard deviations away from the mean of the CTRL distribution, with an average difference in scan-rescan factor of 4%. Notably, the morphological index obtained via a weighted distance method (Koikkalainen factor) had an average difference in scan-rescan factor of less than 1%.

Disease likelihood factor. It will be appreciated by those skilled in the art that a disease evaluation factor is a number that can, depending on the type of calculations and formulas used, be presented as a likelihood ratio. Indeed, because of a change in the formula, applicants can present the disease evaluation factor (DEF) as a disease likelihood factor (DLF) by converting the number used in DEF to a ratio used in DLF. Furthermore, a disease likelihood obtained from the DLF can also be correlated to a disease severity. In such cases, the DLF calculated according to the present invention can also be an indication of disease severity and should be understood as such.

Likelihood ratio. Applicants can use the QPress test, or other test, to determine if the classification results were due to chance or the classification function. Equally, from the a posteriori and a priori probabilities, Applicants can deduce the likelihood ratio:

$P(w_i)$: the a priori probability of belonging to group $w_i$, i=0, 1.

$P(w_i/x)$: the a posteriori probability of choosing x in group $w_i$, i=0, 1.

$P(x/w_i)$: the density of x in $w_i$, i=1, 2. It is the likelihood in $w_i$, i=0, 1.

$$P(x) = P(x/w_0) \cdot P(w_0) + P(x/w_1) \cdot P(w_1). \quad (9)$$

A subject with measure x will be classified in group $w_0$ if $P(w_0/x) > P(w_1/x)$.

Using Bayes' formula, for i=0, 1:

$$P(w_i/x) = \frac{P(x/w_i) \cdot P(w_i)}{P(x)}. \quad (10)$$

The likelihood ratio $\Lambda$ is defined by:

$$\Lambda = \frac{P(x/w_0)}{P(x/w_1)} = \frac{P(w_0/x)}{P(w_1/x)} \cdot \frac{P(w_0)}{P(w_1)}. \quad (11)$$

Hence $$P(w_0/x) > P(w_1/x) \Leftrightarrow \Lambda = \frac{P(x/w_0)}{P(x/w_1)} > \frac{P(w_1)}{P(w_0)}. \quad (12)$$

Thus, a subject is classified as belonging to group 0 if its likelihood ratio is superior to the constant $$\frac{P(w_1)}{P(w_0)}. \quad (13)$$

Discussion. A recent and growing body of literature has used machine learning methods to extract high-dimensional features of interest from MRI, on which classification functions are built to assist in clinical diagnostic of probable AD or predict future clinical status for individuals with MCI (see Kloppel et al, Davatzikos et al., Duchesne et al., Lao, Z., et al., *Morphological classification of brains via high-dimensional shape transformations and machine learning methods*. Neuroimage, 2004. 21(1): p. 46-57; Duchesne, S., et al., *Predicting MCI progression to AD via automated analysis of T1 weighted MR image intensity*. Alzheimer's & Dementia: The Journal of the Alzheimer's Association, 2005. 1(1 (Supplement)): p. 83; Duchesne, S., et al., *Successful AD and MCI differentiation from normal aging via automated analysis of MR image features*. Alzheimer's & Dementia: The Journal of the Alzheimer's Association, 2005. 1(1 (Supplement)): p. 43; Fan, Y., et al., *Spatial patterns of brain atrophy in MCI patients, identified via high-dimensional pattern classification, predict subsequent cognitive decline*. Neuroimage, 2008. 39(4): p. 1731-1743). This work is in line with those approaches. The development of a quantitative, image-based biomarker able to capture disease burden would help monitor disease progression or therapy response.

The gravitational model approach constitutes a novel development in the strategies towards obtaining a single quantitative factor from data reduction and machine learning of very high-dimensional MRI input data towards discrimination of individual subjects. Its inherent flexibility makes multi-group comparisons trivial, alongside the introduction of other sources of data. Its performance compares favorably to other results in the MRI literature within the context of discriminating CTRL vs. probable AD. As a single dimensional scalar, the morphological factor metric achieves strong accuracy (90%), especially when compared to other, multi-dimensional discrimination functions. It is also a strong result when put within the clinical context of discriminating CTRL vs. probable AD, where inclusion evaluations are reportedly 78% accurate (against longitudinal evaluation and final histopathological diagnostic). While lower, accuracy values for the prediction of progression to probable AD in the MCI cohort (on average, 1.5 years before clinical diagnostic) are also strong, and compare favorably to published results on MRI data. A study comparing these approaches (e.g. within a mono-centric setting, such as the Open Access Series of Imaging Studies or multi-centric setting such as the Alzheimer's Disease Neuroimaging Initiative) would be worthwhile.

The paper uses the leave-one-out approach to feature selection (stepwise regression analysis), which allows a correct generalization of the morphological factor as it is not tested on the same data.

Clinical interpretation of changes in image features associated with changes in the morphological factor should provide insight into the development of AD and would need to be compared to existing results from voxel-based morphometry studies, structural studies (e.g. hippocampal and entorhinal atrophy) and histopathological confirmation studies. Overall, Applicants speculate that the specific patterns of intensity and local volume change differences result from different levels of advanced extra-cellular plaque formation, neurofibrillary tangles accumulation and other pathological processes between CTRL and probable AD, and between stable and progressing MCI.

With regards to the features employed in this method, the differences in local volume changes should mirror the changes noticed in other reports, such as visual assessment (Wahlund, L. O., et al., *Visual rating and volumetry of the medial temporal lobe on magnetic resonance imaging in dementia: a comparative study*. J Neurol Neurosurg Psychiatry, 2000. 69(5): p. 630-5), while differences in grey-level might reflect the intensity of neuronal loss induced by the neuropathological changes (Wahlund, L. O. and K. Blennow, *Cerebrospinal fluid biomarkers for disease stage and intensity in cognitively impaired patients*. Neurosci Lett, 2003. 339(2): p. 99-102), which precede volume loss as visualized on MRI.

There are a number of limitations in this study. One pertains to the fact that the MRI images for the probable AD subjects were acquired at the time of diagnosis; therefore, some of the patients have had AD for a number of years. In turn, this implies that extensive neurodegeneration has taken place at this point, and should artificially facilitate the discrimination with CTRL. However, the fact that the latter were age-matched, and the fact that the results in the MCI cohort remain significant, alleviate part of this concern. It would be useful to assess if the morphological factor correlates with different indices of disease severity, cognitive deficits or other biomarkers. Neuropathological confirmation is also required to replace the clinical evaluation as a gold standard. Finally, the patterns of abnormalities that can be found by the method are restricted to a space which is built from healthy, young controls. It is not the optimal space to describe normal aging and/or AD-related variability. However, it does tend to maximize the distance between both groups, as Applicants noticed from building a few reference spaces in a N-fold validation of the CTRL/probable AD groups that achieved lower accuracies.

Figure 6:
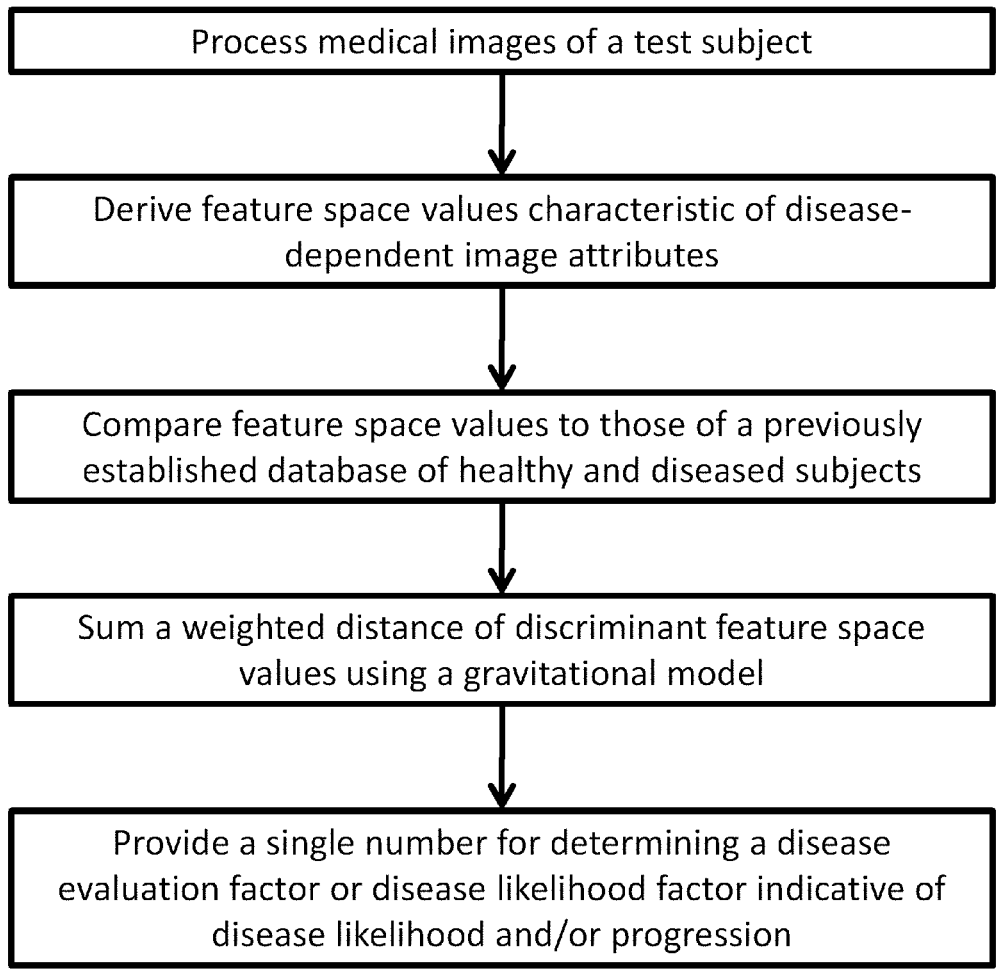
FIG. 6 is a flowchart depicting steps involved in determining a disease evaluation factor or disease likelihood factor.

Applicants estimate that the proposed formulation of the disease evaluation factor and disease likelihood factor is relevant within the context of aid to diagnostic and prediction of future clinical status in probable AD (FIG. 6). Further studies will concentrate on validating the DEF and DLF in a longitudinal setting, and parameters sensibility. Neuropathological confirmation is also required to replace the clinical evaluation as a gold standard.

What is claimed is:

1. A method of quantitatively evaluating a disease likelihood from medical images comprising:
    processing medical images of a test subject to derive feature space values characteristic of disease-dependent image attributes;
    comparing said feature space values to those of a previously established database from medical images of known healthy and known diseased subjects; wherein said comparing is based on feature space values that best discriminate between healthy and diseased subjects;
    summing a weighted distance of discriminant feature space values of said test subject to those of a mean feature space value of said healthy subjects and the mean feature space value of said diseased subjects; and
    providing from said summing a single number which is indicative of disease likelihood, wherein said disease likelihood is calculated from a formula comprising:

$$\Lambda = \frac{P(x/w_0)}{P(x/w_1)} = \frac{P(w_0/x)}{P(w_1/x)} \cdot \frac{P(w_0)}{P(w_1)}$$

where $\Lambda$ is a likelihood ratio;
$P(w_i/x)$ is an a posteriori probability of belonging to group $w_i$, i=0,1.

2. The method according to claim 1, wherein said disease likelihood further comprises providing a likelihood of disease progression.

3. The method according to claim 1, wherein said processing medical images further comprises generating an eigenspace representation of random intensity and spatial morphological features.

4. The method according to claim 1, wherein said disease is Alzheimer's disease.

5. The method according to claim 1, wherein said volume of interest comprises the medial temporal lobe of the brain.

6. The method according to claim 1, wherein said medical images are T1-weighted magnetic resonance imaging (MRI) scans.

7. The method according to claim 1, wherein processing medical images comprises one or more of intensity non-uniformity correction, scaling, global and linear registration.

8. A system for quantitatively evaluating a disease likelihood from medical images comprising:
    an image processor receiving as input a medical image of a test subject and processing said medical image to derive one or more feature space values characteristic of a disease-dependent image attribute;
    a processor comparing said feature space values to those of a previously established database from medical images of known healthy and known diseased subjects; wherein said comparing is based on feature space values that best discriminate between healthy and diseased subjects;
    a processor summing a weighted distance of discriminant feature space values of said test subject to those of the mean feature space value of said healthy subjects and the mean feature space value of said diseased subjects; and
    a calculator providing from said sum a single number which is indicative of disease likelihood;
    wherein said calculator is configured to calculate said disease likelihood using a formula comprising:

$$\Lambda = \frac{P(x/w_0)}{P(x/w_1)} = \frac{P(w_0/x)}{P(w_1/x)} \cdot \frac{P(w_0)}{P(w_1)}$$

where $\Lambda$ is a likelihood ratio;
$P(w_i/x)$ is an a posteriori probability of belonging to group $w_i$, i=0,1.

9. A method of quantitatively evaluating a disease likelihood from medical images comprising:
    processing medical images of a test subject to derive feature space values characteristic of disease-dependent image attributes;
    comparing said feature space values to those of a previously established database from medical images of known healthy and known diseased subjects; wherein said comparing is based on feature space values that best discriminate between healthy and diseased subjects;
    summing a weighted distance of discriminant feature space values of said test subject to those of a mean feature space value of said healthy subjects and the mean feature space value of said diseased subjects; and providing from said summing a single number which is indicative of disease likelihood;

wherein said weighted distance further comprises an attraction field calculation wherein each feature space value of a test subject is attracted to the mean feature space value of healthy and mean feature space value of diseased subjects as a function of its distance from each; and wherein said attraction field calculation comprises:

$$F_{s_i \rightarrow CTRL,AD} = Gm_i \left( \frac{CM_{CTRL}}{d^2_{s_i \rightarrow CM_{CTRL}}} - \frac{CM_{AD}}{d^2_{s_i \rightarrow CM_{AD}}} \right)$$

where $F_{S_i \rightarrow CTRL,AD}$ is a force (F) of attraction between a subject ($S_i$) with a mass ($m_i$) to a center of mass (CM) of CTRL and AD groups;

d is a distance between the subject and the center of mass; and

G is a gravitational constant.

10. A method of quantitatively evaluating a disease likelihood from medical images comprising:

processing medical images of a test subject to derive feature space values characteristic of disease-dependent image attributes;

comparing said feature space values to those of a previously established database from medical images of known healthy and known diseased subjects; wherein said comparing is based on feature space values that best discriminate between healthy and diseased subjects;

summing a weighted distance of discriminant feature space values of said test subject to those of a mean feature space value of said healthy subjects and the mean feature space value of said diseased subjects;

providing from said summing a single number which is indicative of disease likelihood;

wherein a disease likelihood is calculated from a formula of weighted distances comprising:

$$DEF_i = \frac{\sum_i^{\lambda_F} S_F d_i^{\lambda_F}}{\sum_{\lambda_F} S_F}$$

where $\lambda_F$ is a discriminant value;

$S_F$ is a significance weight such that $$S_F = \frac{\ln\,\min[p(\lambda_F), 0.05] - \ln 0.05}{\ln 0.000001 - \ln 0.05}$$

and $$d_i^{\lambda_F} = x_i^{\lambda_F} - \overline{m}_{CTRL}^{\lambda_F}.$$

11. A system for quantitatively evaluating a disease likelihood from medical images comprising:

an image processor receiving as input a medical image of a test subject and processing said medical image to derive one or more feature space values characteristic of a disease-dependent image attribute;

a processor comparing said feature space values to those of a previously established database from medical images of known healthy and known diseased subjects; wherein said comparing is based on feature space values that best discriminate between healthy and diseased subjects;

a processor summing a weighted distance of discriminant feature space values of said test subject to those of the mean feature space value of said healthy subjects and the mean feature space value of said diseased subjects; and a calculator providing from said sum a single number which is indicative of disease likelihood;

wherein said processor is configured to use an attraction field calculation wherein each feature space value of a test subject is attracted to the mean feature space value of healthy and mean feature space value of diseased subjects as a function of its distance from each;

wherein a formula for calculating said attraction field comprises:

$$F_{s_i \rightarrow CTRL,AD} = Gm_i \left( \frac{CM_{CTRL}}{d^2_{s_i \rightarrow CM_{CTRL}}} - \frac{CM_{AD}}{d^2_{s_i \rightarrow CM_{AD}}} \right)$$

where $F_{S_i \rightarrow CTRL,AD}$ is a force (F) of attraction between a subject ($S_i$) with a mass ($m_i$) to a center of mass (CM) of CTRL and AD groups;

d is a distance between the subject and the center of mass; and

G is a gravitational constant.

12. A system for quantitatively evaluating a disease likelihood from medical images comprising:

an image processor receiving as input a medical image of a test subject and processing said medical image to derive one or more feature space values characteristic of a disease-dependent image attribute;

a processor comparing said feature space values to those of a previously established database from medical images of known healthy and known diseased subjects; wherein said comparing is based on feature space values that best discriminate between healthy and diseased subjects;

a processor summing a weighted distance of discriminant feature space values of said test subject to those of the mean feature space value of said healthy subjects and the mean feature space value of said diseased subjects; and a calculator providing from said sum a single number which is indicative of disease likelihood; wherein said calculator is configured to calculate said disease likelihood using a formula of weighted distances comprising:

$$DEF_i = \frac{\sum_i^{\lambda_F} S_F d_i^{\lambda_F}}{\sum_{\lambda_F} S_F}$$

where $\lambda_F$ is a discriminant value;

$S_F$ is a significance weight such that $$S_F = \frac{\ln\,\min[p(\lambda_F), 0.05] - \ln 0.05}{\ln 0.000001 - \ln 0.05}$$

and $$d_i^{\lambda_F} = x_i^{\lambda_F} - \overline{m}_{CTRL}^{\lambda_F}.$$

* * * * *

UNITED STATES PATENT AND TRADEMARK OFFICE
CERTIFICATE OF CORRECTION

PATENT NO. : 8,699,776 B2  
APPLICATION NO. : 13/145646  
DATED : April 15, 2014  
INVENTOR(S) : Simon Duchesne Page 1 of 1

It is certified that error appears in the above-identified patent and that said Letters Patent is hereby corrected as shown below:

Title Page, Item (12) "DUSCHESNE" should be corrected to --DUCHESNE-- and

Item (75) inventor-Simon DUSCHESNE should be corrected to --Simon DUCHESNE--.

Signed and Sealed this  
Eleventh Day of November, 2014

Michelle K. Lee  
*Deputy Director of the United States Patent and Trademark Office*